United States Patent [19]

Poler

[11] 4,450,593
[45] May 29, 1984

[54] INTRAOCULAR AND CONTACT LENS CONSTRUCTION

[75] Inventor: Stanley Poler, New York, N.Y.

[73] Assignee: Lynell Medical Technology Inc., New York, N.Y.

[21] Appl. No.: 319,622

[22] Filed: Nov. 9, 1981

[51] Int. Cl.³ .............................. A61F 1/16; A61F 1/24; G02C 7/04
[52] U.S. Cl. ....................................... 3/13; 351/160 R
[58] Field of Search ....................... 3/13, 1; 351/160 R, 351/160 H, 161, 159

[56] References Cited

U.S. PATENT DOCUMENTS

| | | | |
|---|---|---|---|
| 4,080,709 | 3/1978 | Poler | 3/13 |
| 4,126,904 | 11/1978 | Shepard | 3/13 |
| 4,149,279 | 4/1979 | Poler | 3/13 |
| 4,244,060 | 1/1981 | Hoffer | 3/13 |
| 4,254,509 | 3/1981 | Tennant | 3/13 |
| 4,254,510 | 3/1981 | Tennant | 3/13 |

*Primary Examiner*—Ronald L. Frinks

*Attorney, Agent, or Firm*—Hopgood, Calimafde, Kalil, Blaustein & Judlowe

[57] ABSTRACT

The invention contemplates effectively integral lens-and-haptic structure and a technique of making the same, using composite laminated sheet material as the only ingredient of the ultimate product, which may be an intraocular implant or for extraocular (i.e., cornea-contact) application. The composite sheet material is of substantially the combined ultimate thickness of the lens and haptic, one of the laminations being of a material destined to be substantially only the lens component, and another of the laminations being of a material destined to be substantially only the haptic component. The lens-component lamination may be of optical-quality glass or of a transparent plastic which is inert to body fluids. Suitably coordinated masking and etching steps determine the contour of the ultimate central circular lens as well as the thickness and fenestration detail of the ultimate thin flexible haptic formations which are integral with and extend radially outward of the lens blank. Lens-surface curvature may be developed by conventional grinding techniques or by die compression, as appropriate.

13 Claims, 13 Drawing Figures

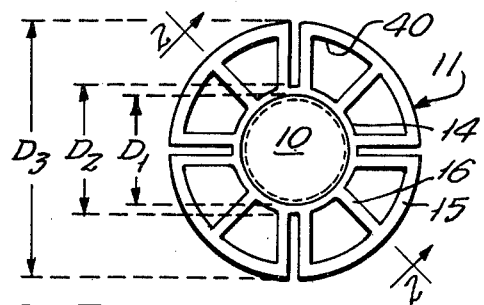
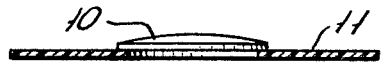
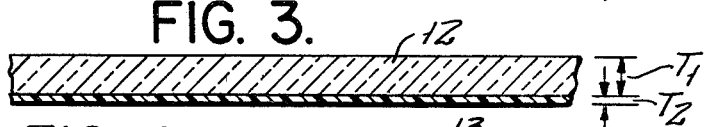
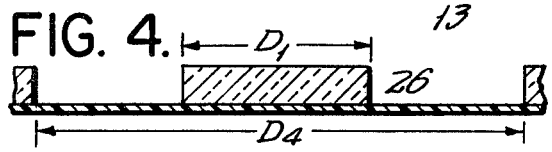
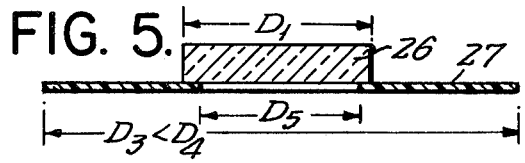
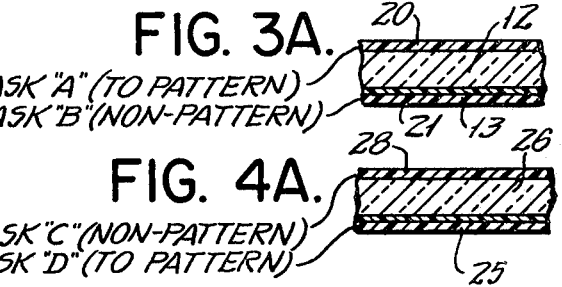
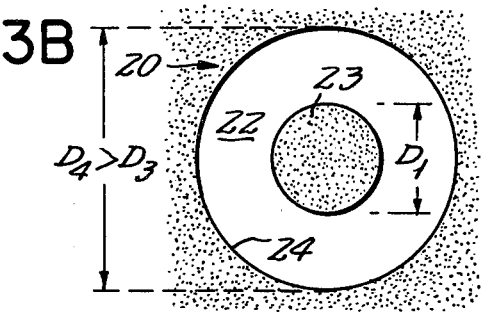
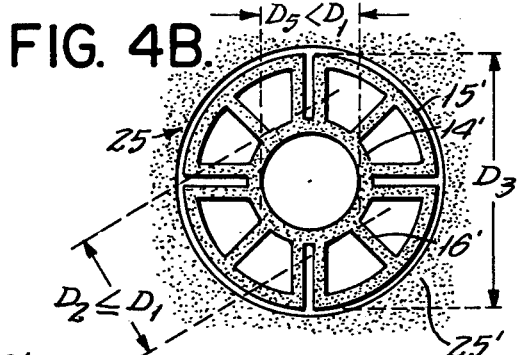
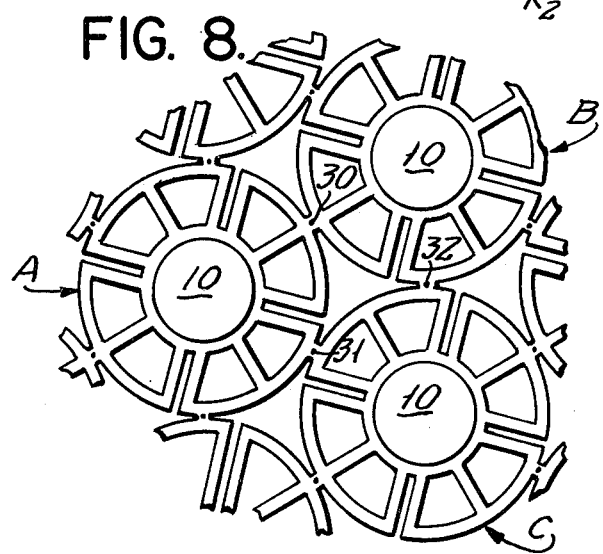
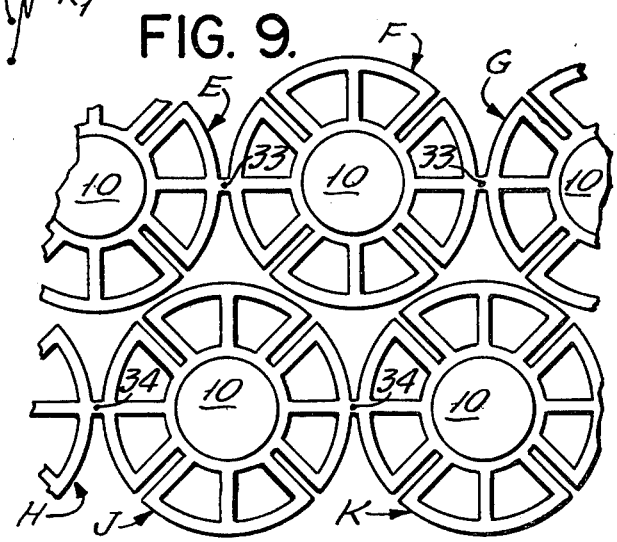

INTRAOCULAR AND CONTACT LENS CONSTRUCTION

BACKGROUND OF THE INVENTION

This invention relates to lens and haptic structures having application as intraocular lens implants, or as extraocular devices for contact application to the cornea, for wear in place of spectacles.

As intraocular devices, such structures and methods of making the same are illustratively treated in my U.S. Pat. No. 4,080,709, and as extraocular devices, such structures are illustratively treated in my U.S. Pat. No. 4,377,329.

Design philosophy behind intraocular and extraocular devices of the character indicated holds that the lens element shall be an optically finished unitary part, and that associated haptic structure shall be a separate thin flexible part or parts devised and assembled for central support of the lens element and for suitably compatible stabilized referencing engagement with adjacent body features.

There is another category of intraocular lens, exemplified by Choyce, et al., U.S. Pat. No. 4,087,866, wherein lens and haptic structure are the integral product of plastic-molding. But such products do not lend themselves to fabrication with glass, nor to known glass-lens finishing techniques. Moreover, injection-molded plastic materials are inherently incapable of providing the optical quality and uniformity that is available from glass and from certain plastic materials which are available in flat-sheet form.

My copending application, Ser. No. 288,217, filed July 29, 1981, now U.S. Pat. No. 4,402,579, is concerned with structures and methods, involving intraocular and extraocular devices of the character indicated, wherein the starting material is a single flat sheet of glass or suitable plastic, and the present application is concerned with similar devices wherein the starting material is a composite laminate of different materials.

BRIEF STATEMENT OF THE INVENTION

It is an object to provide improved integrally formed lens and haptic structures of the character indicated, specifically involving composite laminated starting material.

A specific object is to provide such structures from a starting composite laminate wherein one lamination is optimized for its optical properties and another lamination is optimized for supporting haptic purposes.

A specific object is to meet the above objects with structures and techniques which utilize flat composite laminated sheet material as the starting and only material of the ultimate product.

The invention achieves these objects and certain further features by employing suitably coordinated masking and etching steps to determine in one of at least two composite laminations the peripheral contour of the ultimate central lens and in another of the laminations the thickness and fenestration detail of the ultimate thin flexible haptic formations; since these lens and haptic formations are from laminated starting materials; the haptic formations remain effectively integral with and extend radially outward of the lens blank. In all cases, the starting material is flat composite laminated-sheet stock, of thickness to provide for the overall ultimate axial extent of the lens. Lens-surface curvature may be developed prior to but is preferably developed after haptic formation. The masking and fenestration detail are provided via photo-etch techniques and are applicable to mass production of plural duplicates of the identical lens-and-haptic structures from a single composite laminated sheet, through formative operations performed concurrently and in common on all structures of a given sheet.

DETAILED DESCRIPTION OF THE INVENTION

Illustrative structures and techniques of the invention will be described in detail in conjunction with the accompanying drawings, in which:

FIG. 1 is a plan view of a single-piece effectively integrally formed lens and haptic construction of the invention;

FIG. 2 is an enlarged sectional view, taken at 2—2 in FIG. 1;

FIG. 3 is a further-enlarged schematic sectional representation of sheet of composite laminated starting material, for the aspect depicted in FIG. 2, i.e., what begins as shown in FIG. 3 ultimately becomes what is shown in FIG. 2;

FIGS. 4 and 5 are diagrams similar to FIG. 3, to show the result of different intermediate steps in proceeding from the material of FIG. 3 to the product of FIG. 2;

FIGS. 3A and 4A are sectional views, and FIGS. 3B and 4B are diagrammatic representations to show use of different masks to create the respective intermediate stages of FIGS. 4 and 5;

FIGS. 6 and 7 are views similar to FIGS. 4 and 5, to illustrate two different finishing steps for the product of FIGS. 1 and 2; and FIGS. 8 and 9 are similar fragmentary plan views of two alternative multiple-structure layouts on a single sheet of starting material, for mass-production purposes.

In the form of FIGS. 1 and 2, the invention is shown in application to an extraocular or contact-lens assembly, strongly resembling multiple-component structure as disclosed in my said U.S. Pat. No. 4,377,329 but in reality comprising a central lens 10 and haptic structure 11 which are effectively integral with each other, being the product of selectively etched reduction from starting material in the form of flat composite laminated sheet stock, of thickness $T_1 + T_2$, as shown in FIG. 3, wherein $T_1$ is the thickness of one (12) of the composite laminations (shown for glass) and $T_2$ is the thickness of the other (13) of the composite laminations (shown for plastic). The lamination 12 is of thickness to permit ultimate lens formation therefrom, and the lamination 13 is of thickness to serve ultimate haptic formation therefrom; the composite laminated stock is selected for inertness to body fluids.

For convenience, dimensional symbols have been applied to identify: lens 10 diameter at $D_1$, which may be in the range of 6 to 9 mm; an inner circumferential haptic band or ledge 14, which is preferably at least 0.40-mm wide, to account for its outer diameter $D_2$ in the range of 6.5 to 9.5 mm; with retained bonded lap to the rim of lens 10; and haptic outer diameter $D_3$ which may be in the range up to 20 mm, and thus in excess of the 12 to 14 mm diameter of the iris of an eye. It will be understood that haptic 11 may be characterized by very substantial fenestration, meaning that the structure is primarily "open", for normal air or "breathing" exposure of the surface of the cornea to which it is applied. Such substantial fenestration is shown and described in said U.S. Pat. No. 4,377,329, and is therefore not repeated here. It suffices to note that the detail of fenestration and the varieties of haptic configuration of said U.S. Pat. No. 4,377,329 are achievable for the techniques and structures to be described herein; therefore, such detail is not here repeated. It is also to be noted that the detail of haptic configuration and size, for intraocular-lens application, including lens size and power appropriate to intraocular use, may be achieved with the invention, so that dimensions and shapes given herein for the extraocular situation are to be regarded as merely illustrative and not limiting.

It suffices here to describe the haptic 11 as comprising four arcuate feet 15, connected to each other and to lens element 10 only via integral radial legs 16 to ledge 14. Lens thickness $T_1$ is generally in the range 0.001 to 0.007 inch, for extraocular applications, and in the range of 0.002 to 0.020 for intraocular applications; and haptic thickness $T_2$ (FIG. 3) is in the order of 0.001 to 0.006 inch for both applications.

To proceed from the sheet 12 of FIG. 3 to the intermediate stage of FIG. 4, I utilize mask and photo-etch techniques which are illustratively described in my U.S. Pat. No. 4,080,709 and which therefore need not be repeated here. It suffices to indicate that for present purposes, a mask as in FIG. 3B is used for the chemical or other etching of the upper lamination 12 of the composite sheet and that a different mask as in FIG. 4B is used for such etching of the lower lamination 13 of the composite sheet. These two different etchings preferably proceed separately (e.g., sequentially), thereby achieving full control of the particular depth of erosion desired from each lamination of the composite sheet.

More specifically, the mask pattern of FIG. 3B may be a precise photographic reduction from a master drawing, the reduction being to expose a photosensitive coating of the upper surface of the composite sheet, the exposed coating being thereafter developed to leave a deposited opaque masking pattern 20 (Mask A) on lamination 12 of the composite sheet. Since it is my preference first to etch from one side and then from the other, I fully expose the photosensitive coating on the lower surface of sheet 12, so that upon development, the lower surface is an entirely opaque mask 21 (Mask B) and is thus incapable of permitting an etch from the lower side. With the thus-masked sheet then exposed to an etching environment (for the material of lamination 12), only the areas not opaquely masked will be etched, and this first etching is timed for full penetration of lamination 12 (i.e., to the depth $T_1$), thus leaving only lamination 13, of haptic thickness $T_2$, in the etched region. As seen in FIG. 3B, this first mask is characterized for etching exposure of the circular annulus 22, defined internally by a lens-size opaque circular area 23 of diameter $D_1$ and on the outside by a circumferentially enveloping opaque area. The outer opaque area has a circular inner edge 24 of diameter $D_4$ slightly greater than ultimate haptic diameter $D_3$. The product of thus-masked etching is depicted in FIG. 4.

Having etched through the mask 20 of FIG. 3B to the indicated depth $T_1$, all maskings are stripped and the specimen is recoated with photosensitive material. The mask pattern 25 of FIG. 4B is then exposed and developed on the underside of the specimen (becoming Mask D in FIG. 4A), in precise concentric relation with the FIG. 3B exposure and etching, while the upper surfaces of the central lens-blank region 26 and surrounding annular haptic area 27 are totally exposed and developed to produce an unpatterned mask 28 (Mask C) and thus to enable etching exposure (appropriate to the material of lamination 13) only through the FIG. 4B mask (Mask D) on the lower surface of the specimen. This second etching is allowed to proceed fully through the material of lamination 13 (i.e., through ultimate haptic thickness $T_2$), at which time the intermediate product of FIG. 5 becomes severed from surrounding original sheet material. It is, of course, possible then to strip maskings from the specimen and to proceed thence with lens-finishing. However, it is my preference that the mask of FIG. 4B be formed with at least one later-severable tie-forming opaque connection between the fenestration-defining inner pattern (within diameter $D_3$) and the inner-edge diameter $D_4$ of surrounding opaque region 25' of the pattern mask 25.

The inner pattern of the mask 25 of FIG. 4B, i.e., within the diameter $D_4$ of the inner circular edge of surrounding opaque material 25', will be seen to have the haptic-fenestration detail described in connection with FIG. 1, and therefore in FIG. 4B corresponding inner opaque parts of this mask (Mask D) are given FIG. 1 reference numbers, with primed notation. However, in the mask of FIG. 4B, the full area within the inner circular confines of ledge 13, i.e., within a circle of diameter $D_5$ is open, diameter $D_5$ being less than the diameter $D_1$ of the lens blank 26, to assure an annulus of retained composite lamination between the etched lens blank 26 and the etched haptic 27.

Having performed the second etch to the pattern of FIG. 4B, all mask deposits are stripped from the partially completed specimen, to permit lens-finishing. In the individually separated specimen situation, each item must be separately handled, but in the edge-interconnected situation, the individual specimens may be more readily handled by mass lens-finishing techniques. One pattern of edge-interconnected specimens is illustrated in FIG. 8, wherein each partially completed specimen (per FIG. 5) is in nested adjacency to and interconnected with six surrounding like specimens; in the fragmentary showing of FIG. 8, three thus-nested partially completed specimens A-B-C are connected, as by a severable tie 30 between specimens A and B, by a severable tie 31 between speciments A and C, and by a severable tie 32 between specimens B and C.

FIG. 9 is a diagram similar to FIG. 8, but showing a different pattern of severable interconnection of partially completed specimens, also lending itself to mass-production handling in lens-finishing phases of production, as will later become more clear. In FIG. 9, the pattern of severable interconnection is on discrete parallel alignments of connection. For example, the partially completed specimens E-F-G of one such alignment are severably interconnected at 33 to each other, and the partially completed specimens H-J-K of the next adjacent such alignment are severably interconnected (at 34) but are not connected to the specimens of alignment A-B-C or to those of any other alignment. In other words, the arrangement of FIG. 9 permits automated handling of linear arrays of severably connected specimens.

Returning now to the matter of lens-finishing, and taking the case of having performed etching steps on a starting sheet wherein the lamination 12 is of suitable plastic, the partially completed specimen of FIG. 5 is first accurately positioned in a forming die. Then, the lens shape which may involve an inner concave surface of radius $R_1$ and an outer convex surface of different radius $R_2$ (see FIG. 7), is established by plastic deformation under elevated compressional pressure within the die, resulting in a finished product, as shown in FIG. 7. In this particular finished product, it will be noted that the convex anterior surface of lens 10 is offset from the ledge 13 of effectively integral haptic 11 connection, and that the posterior surface of lens 10 is effectively flush with the haptic, since the haptic thickness $T_2$ is very small compared to lens thickness $T_1$.

Although it has been indicated that if the lens-material lamination 12 is a plastic or one of the low-temperature forming glasses, one can compression-form desired curvature(s) in the etched lens blank (26), it is my preference that recognized optical-finishing techniques be employed in the finishing of effectively integral lens-and-haptic configurations wherein the lens-defining lamination 12 is of glass. FIGS. 14, 15 and 16 of my said copending application Ser. No. 288,217 (U.S. Pat. No. 4,402,579) illustrate lens-grinding apparatus suitable for finishing a glass blank 26 and therefore such apparatus need not now be further described.

Briefly, a partially completed etched product, as in FIG. 5, comprises a lens blank portion 26 of glass and an effectively integrally associated haptic portion 27, and the latter is sufficiently thin to be axially compliant. The flat blank region 26 is mounted to a suitable platform location of a conventional generally truncated spherical multiple-blank support, being removably affixed thereto by wax embedment in accordance with accepted practice, and by wax being also used to removably retain the flexible haptic portions 27 in conformance to curved surfaces of support, adjacent the platform locations. The curvature of radius to which haptic features are thus temporarily conformed is less than or at least relieved from the local of ultimate convex grinding curvature $R_2$ to which the anterior surface of blank 26 is to be ground. For such grinding, a master grinding member having a concave master-grind curvature of radius $R_2$ performs a conventional grinding of the convex anterior lens surface, to radius $R_2$.

As also explained in said copending application, Ser. No. 288,217 (U.S. Pat. No. 4,402,579), the lens-mounting flat platforms of the lens-grinding support may be at spacings and alignments appropriate to the multiple mounting of severably connected partially completed specimens, for example, a longitudinally connected array as described in connection with FIG. 9. In that event, each of the lens blanks (26) of the connected array will have its own flat mounting platform, and all blanks 26 and their haptics 27 will be removably fixed by wax, in position for grinding in unison against the master grinding member, all to the same convex curvature $R_2$. Each resulting effectively integral lens-and-haptic product, after grinding against the master, will then have the unit appearance depicted in FIG. 6, with a plano-convex lens 10', once the wax connection is dislodged by heat.

As further explained in said copending application, Ser. No. 288,217 (U.S. Pat. No. 4,402,579), conventional glass-lens finishing techniques are also applicable to the generation of concave surfaces, as to radius $R_1$ on the posterior surface of the structure of FIG. 6, resulting in a lens 10" as depicted in FIG. 7.

It will be understood that described processes and structures meet the above-stated objects, and that they are applicable in the context of a variety of composite laminate materials and finishing techniques. For example, in the event of a glass-to-plastic composite, the glass lamination 12 should be of optical quality material, and the haptic lamination 13 may be selected from available polyimides and polyamides, as well as porous polymethylmethacrilate (HEMA), polyethersulfone, polysulfone, polymethylmethacrilate (PMMA), polyesters, silicones, and polyethyltoluene (PET).

Also by way of example, conventional techniques may be employed to build astigmatism-corrective curvatures and axial orientation into the effectively integral haptic and lens structure, complete with a recognition profile or the like from which correct astigmatic-correction axis orientation can be recognized by the physician prescribing and/or installing the structure. Such orientation-refining techniques are described in my copending application, Ser. No. 225,349 (filed Jan. 15, 1981), and in FIG. 1, I show by phantom outline 40 that a small asymmetrical fillet may locally characterize fenestration detail, thereby providing the means of recognizing correct orientation to achieve proper use of the astigmatism-correcting lens prescribed for the particular user.

The reference to etching herein is to be understood as contemplating any of various well recognized selective erosion techniques. For the case of plastic erosion, these techniques include plasma etching, ion milling, and chemical etching. For the case of glass erosion, these techniques include hydrofluoric-acid etching and hydrofluoric-gaseous etching.

While the invention has been described in detail for various illustrative forms and processes, it will be understood that modifications may be made without departing from the scope of the invention.

For example, in either of the techniques illustrated by FIGS. 8 and 9, the severable tie elements 30-31-32 (33-34) may be characterized by a central "pin-hole" opening external to the perimeter of each of the haptics thereby connected. Such a pin-hole opening is illustratively shown at 30 in FIG. 8 and will be understood, in context with other such pin-hole openings (i.e., at other severable connections) to provide a precise optically scannable reference, as when automatically positioning a severably connected array of etched lens blanks with haptics, the positioning being for accurate placement in a multiple-lens press, and/or for precise automated laser cut-off of completed lens-haptic units 10-11 from the array.

Further, it will be understood that the lens-pressing and lens-grinding operations described are purely illustrative, in that not only may astigmatism-corrective curvature be embodied in the pressing die, but so also may other complex curvatures, as for example the curvatures which will embody multifocal (e.g., bi-focal, tri-focal) properties in the lens-blank lamination.

Still further, although the described selective etching steps have been stated to be for times appropriate to achieve etching to stated depths $T_1$ and $T_2$, as the case may be, it will be understood that with suitable choice of different etching environments for the different lamination materials involved, the timing of etching steps may not be critical. For example, for the case of a glass lamination 12 and for a plastic lamination 13 that is sensitive to sodium hydroxide, the glass etch may be via a hydrogen fluoride to which the plastic lamination is not sensitive, and the plastic etch may be via sodium hydroxide (to which the glass lamination is not sensitive). In such case, it will be appreciated that each etching operation is selectively operable only upon the lamination material which is sensitive to the applicable etching environment, so that an excess timing of either etch is not harmful to the lamination which is not then intended to be etched.

For purposes of simplified presentation, the foregoing description has dealt with the laminations 12-13 of the composite starting sheet as if each lamination were a homogeneous solid, but it will be appreciated that, particularly in extra-ocular applications, a degree of gas and fluid permeability is desired, for enhanced compatability with the human eye. Some of the above-indicated plastic materials exhibit a degree of such permeability, but I prefer to employ exposure to ion, neutron or other particle or X-ray bombardment, as a means of creating a desired mix of holes and hole sizes to thereby enhance permeability, the bombardment being preferably a controlled step applied to the composite sheet, prior to the erosion processes described above; alternatively, the bombardment to enhance permeability may be performed after masking and just before etching, or after the lens-finishing step. To provide a degree of gas and fluid permeability for applications in which glass is used rather than plastic, it can be noted that glasses with such permeability now exist and are available from Corning Glass Works, Corning, N.Y.

Also, for simplified presentation, the description of the invention has been concerned primarily with the lens element and its formation, so that it will be understood that conventional optical coating and other finishing steps desired for other lens configurations are equally applicable for the present case. Another such finishing step may be a third etch (without mask) to improve edge geometry and avoid sharp edges in the final product.

What is claimed is:

1. A unitary lens and haptic construction integrally formed from the same single composite continuously laminated sheet of two different uniformly thick ply materials at least one of which materials is transparent and of optical quality and constitutes a relatively thick rigid first ply of said single sheet, the other ply material of said single sheet being relatively thin compared to the thickness of said first ply, said construction comprising a relatively thick rigid central lens component peripherally eroded exclusively from said first ply material to a generally circular periphery of lens-component diameter ($D_1$), and a relatively thin pliant generally annular outer haptic component having a central opening concentric with said lens component and peripherally eroded exclusively from said other ply material to a diameter ($D_5$) which is less than the diameter ($D_1$) of said lens component, whereby said haptic component is in concentric peripherally continuous retained laminated overlap with one side of the rim region of said lens component, said haptic component comprising plural leg formations radiating from the lens periphery at angular offset from each other.

2. The construction of claim 1, wherein the lens-component diameter is in the range of 6 to 9 mm.

3. The construction of claim 1, wherein the haptic-component thickness is in the order of one thousandth of an inch.

4. The construction of claim 1, wherein said construction is one of a plurality of like constructions in laterally offset relation and formed from the same single laminated sheet, being integrally but severably joined to each other at local proximity of their respective haptic components.

5. The construction of claim 4, wherein a short integrally formed tie between adjacent haptic components is the means of severable connection.

6. The construction of claim 1, in which said first ply is of glass, and said other ply is of plastic.

7. The construction of claim 1, in which said first ply is of a first plastic material and said other ply is of a second plastic material.

8. The construction of claim 1, in which said composite laminated sheet is transparent.

9. The construction of claim 1, wherein the pattern of haptic formations includes an observable asymmetric indicium which establishes a recognizable reference orientation, and wherein the central lens component includes an astigamtic-correction curvature having an axis orientation of predetermined angular orientation with respect to said reference orientation.

10. The construction of claim 6, in which the glass ply is gas and fluid permeable.

11. The construction of claim 6 or claim 7, in which the plastic is gas and fluid permeable.

12. A unitary lens and haptic construction integrally formed from the same single composite continuously laminated sheet of two different uniformly thick ply materials at least one of which materials is transparent and of optical quality and constitutes a relatively thick rigid first ply of said single sheet, the other ply material of said single sheet being relatively thin compared to the thickness of said first ply, said construction comprising a relatively thick rigid central lens component peripherally eroded exclusively from said first ply material to a generally circular periphery of lens-component diameter ($D_1$), and a relatively thin pliant generally annular and radially outwardly extending haptic component formed exclusively of said other ply material, said haptic component having a central opening concentric with said lens-component and peripherally eroded from said other ply material to a diameter ($D_5$) which is less than the diameter ($D_1$) of said lens component, whereby said haptic component is in concentric peripherally continuous retained laminated overlap with one side of the rim region of said lens component.

13. A unitary lens and haptic construction integrally formed from the same single composite laminated sheet of two different materials at least one of which materials is transparent and of optical quality and constitutes a relatively thick rigid first ply of said single sheet, the other ply material of said single sheet being relatively thin compared to the thickness of said first ply, said construction comprising a relatively thick rigid central lens component formed exclusively of said first ply material and having a generally circular periphery, and a relatively thin pliant generally annular outer haptic component formed exclusively of said other ply material in peripherally continuous retained laminated overlap with at least the rim region of said lens component, said haptic component comprising plural leg formations radiating from the lens periphery at angular offset from each other; said construction being one of a plurality of like constructions in laterally offset relation and formed from the same single laminated sheet, said like constructions being integrally but severably joined to each other via a short integrally formed tie between adjacent haptic components, each tie having a locating aperture in a region external to the peripheral contour of each of the adjacent haptics thereby severably joined, whereby lens blanks associated with the severably connected haptics may be accurately positioned via such apertures, as for lens-finishing alignment and orientation, and for cut-off.

* * * * *

UNITED STATES PATENT AND TRADEMARK OFFICE
CERTIFICATE OF CORRECTION

PATENT NO. : 4,450,593
DATED : May 29, 1984
INVENTOR(S) : Stanley Poler

It is certified that error appears in the above—identified patent and that said Letters Patent is hereby corrected as shown below:

Correct title to read:

-- INTRAOCULAR AND EXTRAOCULAR LENS CONSTRUCTION AND METHOD OF MAKING THE SAME --

Signed and Sealed this

Sixteenth Day of October 1984

[SEAL]

*Attest:*

*Attesting Officer*

GERALD J. MOSSINGHOFF

*Commissioner of Patents and Trademarks*